United States Patent [19]
Dahn et al.

[11] Patent Number: 5,520,178
[45] Date of Patent: May 28, 1996

[54] SELF-GUIDING, MULTIFUNCTIONAL VISCERAL CATHETER

[75] Inventors: Michael S. Dahn, Farmington Hills, Mich.; M. Patricia Lange, 32209 Hull, Farmington Hills, Mich. 48336

[73] Assignee: M. Patricia Lange, Farmington Hills, Mich.

[21] Appl. No.: 332,715

[22] Filed: Nov. 1, 1994

[51] Int. Cl.$^6$ ........................................................ A61B 5/00
[52] U.S. Cl. ........................ 128/637; 128/642; 128/692; 604/264
[58] Field of Search ............................ 604/264, 270, 604/280–282; 128/637, 639, 642, 654, 656, 657, 658, 691, 692, 772

[56] References Cited

U.S. PATENT DOCUMENTS

| | | | |
|---|---|---|---|
| 4,853,091 | 8/1989 | Mund et al. | 128/637 |
| 4,882,492 | 11/1989 | Schlager | 128/637 |
| 4,957,110 | 9/1990 | Vogel et al. | 128/642 |
| 5,184,621 | 2/1993 | Vogel et al. | 128/642 |
| 5,372,133 | 12/1994 | Hogen Esch | 128/642 |

OTHER PUBLICATIONS

Michael Dahn, M. D., F.A.C.S., Patricia Lange, B.S.N., C.C.R.N. et al., "Splanchnic and total body oxygen consumption differences in septic and injured patients", Surgery, vol. 101, No. 1, pp. 69–80 (1987).
Michael S. Dahn, M.D., M. Patricia Lange, MSN, et al., "Hepatic blood flow and splanchnic oxygen consumption measurements in clinical spesis", Surgery, Vo. 107, No. 3, pp. 295–301 (1990).
Christopher P. Stettes, MD; Michael S. Dahn, MD, PhD; M. Patricia Lange, Phd, "Oxygen Transport–Dependent Splanchnic Metabolism in the Sepsis Syndrome", Archives of Surgery, vol. 129, pp. 46–52 (1994).
Michael S. Dahn, MD, PhD, "Hepatic Dysfunction in the critically ill and injured", Intensive Care World, 11: 9–14 (1994).
John M. Sperinde, PhD, Kathi M. Senelly, BS, "The oximetrix opticath oximetry system: Theory and development", Oximetrix, Inc., pp. 59–79.
Terry Lumsden, BS; William Marshall, BS, et al., "The PB3300 intraarterial blood gas monitoring system", Knowing Your Monitoring Equipment, Journal of Clinical Monitoring, vol. 10, No. 1, pp. 59–66 (1994).
Mathias Haller, MD; Erich Kilger, MD. et al., "Continuous intra–arterial blood gas and pH monitoring in critically ill patients with severe respiratory failure: A prospective, criterion standard study", Critical Care Medicine, Vo. 22, No. 4, pp. 580–587 (1994).

*Primary Examiner*—Corrine M. Maglione
*Assistant Examiner*—N. Kent Gring
*Attorney, Agent, or Firm*—Weiner, Carrier & Burt; Pamela S. Burt; Irving M. Weiner

[57] ABSTRACT

A multifunctional visceral catheter having a self-guiding system in the form of a pair of electrochemical sensors which are sensitive to a predetermined analyte, the analyte being one which is removed from the vascular circuit of interest to a high degree, such as galactose in the hepatic venous system or creatinine in the renal venous system. One of the sensors is disposed on the catheter so as to be positioned within the venous system of interest, while the other sensor remains outside the venous system in the inferior vena cava. A substantial difference between analyte concentration values as measured via the two sensors provides immediate confirmation that the catheter is properly positioned, eliminating the need for fluoroscopy or other x-ray techniques. In addition to being self-guiding, the catheter provides for direct sampling of venous blood; is capable of continuously monitoring oxygen saturation in the hepatic or renal venous blood; and is capable of measuring absolute hepatic or renal blood flow using a tracer clearance technique.

20 Claims, 3 Drawing Sheets

SELF-GUIDING, MULTIFUNCTIONAL VISCERAL CATHETER

BACKGROUND OF THE INVENTION

1. Field of the Invention

The present invention relates generally to a multifunctional visceral catheter which is substantially self-guiding, i.e., which may be positioned in a visceral venous system without the need for bedside fluoroscopy or other x-ray devices.

More particularly, the self-guiding system of the catheter according to the invention comprises sensor systems which are sensitive to an analyte or metabolite having a substantial extraction fraction across the splanchnic bed or vascular circuit being explored. When the catheter is properly positioned, such as in the hepatic or renal vein, the first sensor system will yield signals reflecting a substantially higher concentration of the given analyte or metabolite than will a second sensor system positioned in the hepatic or renal venous system, thus readily confirming proper positioning of the catheter.

The catheter according to the invention is also capable of performing various monitoring and assessment functions. The catheter is capable of continuously monitoring the oxygen saturation in the hepatic or renal venous blood once the catheter is placed in any major hepatic or renal venous vessel. The catheter according to the invention also has the capability of measuring absolute hepatic or renal blood flow using a tracer clearance technique. Further, the catheter permits direct sampling of venous blood, such as hepatic or renal venous blood, for the ex vivo measurement of metabolite concentrations.

2. Description of Relevant Art

Known methods of diagnosing liver and/or kidney dysfunction, as well as assessing various physiological parameters associated with the functioning of these organs, typically require catheterization of the hepatic or renal venous systems. A principal disadvantage associated with known techniques for catheterizing the hepatic and renal venous systems is that bedside fluoroscopy or other x-ray devices are required in order to properly position the catheter. For example, while a thermodilution catheter has been developed for renal blood flow determination which might be applicable to general clinical use, the need for fluoroscopic assistance in positioning such catheter is a critical shortcoming. See M. Brenner, G. L. Schaer, D. L. Mallory, et al, "Detection of renal blood flow abnormalities in septic and critically ill patients using a newly designed indwelling thermodilution renal vein catheter", *Chest*, Vol. 98, pp. 170–79 (1990).

The present invention overcomes this major shortcoming of known catheterization techniques by providing a visceral catheter which is effectively self-guiding, i.e., which permits positioning of the catheter in either the hepatic or the renal venous systems without the use of bedside fluoroscopy or other x-ray devices.

In addition to this novel self-guiding feature, the multifunctional visceral catheter according to the invention also permits continuous monitoring of the oxygen saturation in the hepatic or renal venous blood. Heretofore, there has been no known technique for readily assessing individual organ oxygenation. Instead, central mixed venous oxygen saturation has commonly been used as an index of global body oxygenation, without any assessment of individual organ function or oxygenation. However, the results of various studies have shown that a marked reduction in hepatic venous oxygen saturation frequently exists in critically ill patients. See, e.g., Michael S. Dahn, M. Patricia Lange, Robert F. Wilson, Lloyd A. Jacobs, and Robert A. Mitchell, "Hepatic blood flow and splanchnic oxygen consumption measurements in clinical sepsis," *Surgery*, Vol. 107, No. 3, pp. 295–301 (March 1990). This condition goes undetected when only global body oxygenation is assessed, leaving the physician unaware of a condition which could otherwise be therapeutically addressed through the use of cardioactive drugs or blood transfusion. To overcome this problem, the multifunctional visceral catheter according to the present invention is capable of continuously monitoring regional oxygenation. Thus, once the catheter according to the invention is placed in a major hepatic vessel, hepatic function can be assessed in a more direct fashion than is possible by conventional means, such as by monitoring serum bilirubin or liver enzymes.

Similarly, the novel catheter according to the invention permits convenient, direct monitoring of the renal venous system. By positioning the catheter according to the invention in the renal vein, endogenous creatinine clearance and other renal functional indicators can be critically assessed. Further, if inulin and/or para-aminohypurate are available for intravenous infusion, glomerular filtration rate and renal blood flow can be assessed.

SUMMARY OF THE INVENTION

The present invention provides a visceral catheter comprising a main catheter body provided with means for guiding the catheter to a position in which a portion of the main body is disposed within a predetermined visceral venous system. The guiding means comprises first sensor means for detecting values of a predetermined analyte and for outputting signals related thereto, the first sensor means being disposed on a first portion of the main catheter body which is adapted to remain outside the visceral venous system; and second sensor means for detecting values of the predetermined analyte and for outputting signals related thereto, the second sensor means being disposed on a second portion of the main catheter body which is adapted to be positioned within the visceral venous system. The predetermined analyte has a specific relationship to the organ associated with the predetermined visceral venous system such that values of the analyte within the visceral venous system are substantially different from systemic values of the analyte outside the visceral venous system. The first and second sensor means are selectively connected to detector means for comparing the signals from the first and second sensor means and for alerting a user to a substantial difference between the signals.

In a preferred embodiment, the main catheter body comprises a main axial portion extending from the proximal end thereof, and an angled distal end portion extending from the main axial portion at an acute angle, such as an angle of substantially 65°. The first and second sensor means each comprises an electrochemical sensing system including an electrode with a hydratable membrane containing a reagent which detects values of the predetermined analyte.

It is an object of the invention to provide a visceral catheter which may be readily positioned within the hepatic or renal venous system by virtue of a novel self-guiding sensor arrangement which utilizes the difference in concentration of a given analyte within the visceral venous system, as opposed to outside that venous system, to readily confirm proper positioning of the catheter.

A further object of the invention is to provide a self-guiding visceral catheter comprising means for continuously monitoring the oxygen saturation of blood in a desired visceral venous system, the monitoring means taking the form of a fiber optic system including a fiber optic cable extending along an inside surface of the catheter.

Another object of the invention is to provide a visceral catheter having the capability of measuring absolute hepatic or renal blood flow using a tracer clearance technique, with such measurement being based on outputs from the same sensor systems which form part of the self-guiding system of the catheter.

The above and further objects, details and advantages of the invention will become apparent from the following detailed description, when read in conjunction with the accompanying drawings.

DETAILED DESCRIPTION OF PREFERRED EMBODIMENTS

Figure 1:
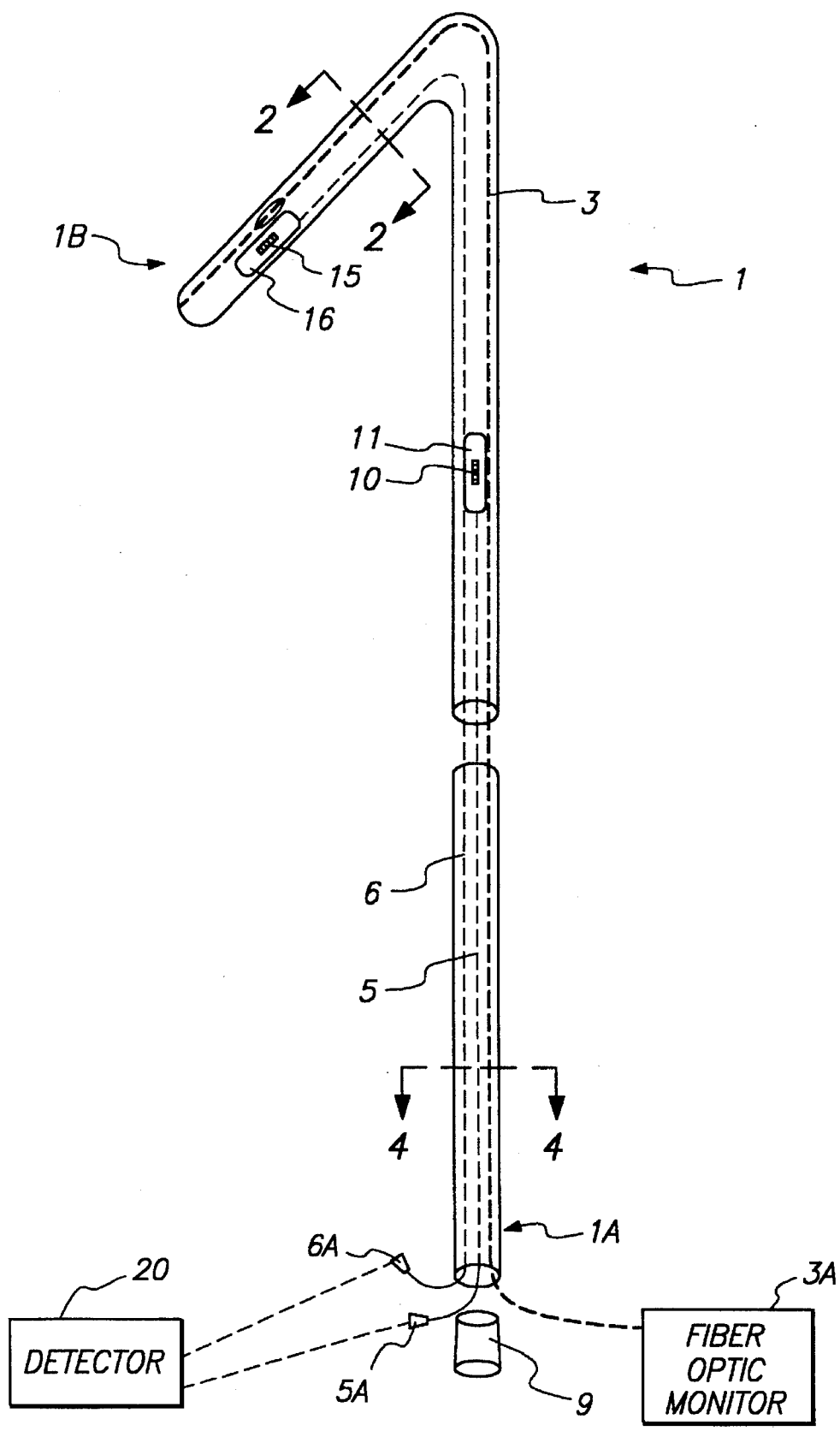
FIG. 1 depicts a schematic perspective view of a preferred embodiment of the multifunctional visceral catheter according to the invention.

With reference to FIG. 1, the self-guiding, multifunctional visceral catheter 1 according to the invention comprises a main body having a proximal end 1A and a distal end 1B. In a preferred embodiment, the catheter 1 may preferably comprise a 7F polyvinyl chloride diagnostic catheter which is designed for passage through an introducer system via the transfemoral venous route.

The distal end portion of catheter 1 is bent at an acute angle to facilitate spontaneous engagement of the distal end of catheter 1 with a desired vein during positioning, as described in greater detail below. In a preferred embodiment, the portion of catheter 1 including distal end 1B is disposed at an angle of substantially 65° relative to the main axial portion of the catheter which includes proximal end 1A, although the acute angle may be varied as necessary depending upon the particular application.

Figure 2:
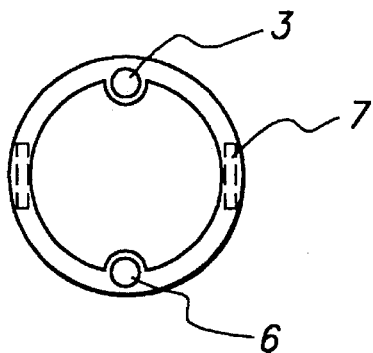
FIG. 2 is a cross-sectional view taken along line 2—2 in FIG. 1.
Figure 4:
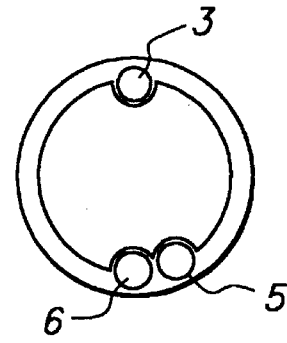
FIG. 4 is a cross-sectional view taken along line 4—4 of FIG. 1.
Figure 3:
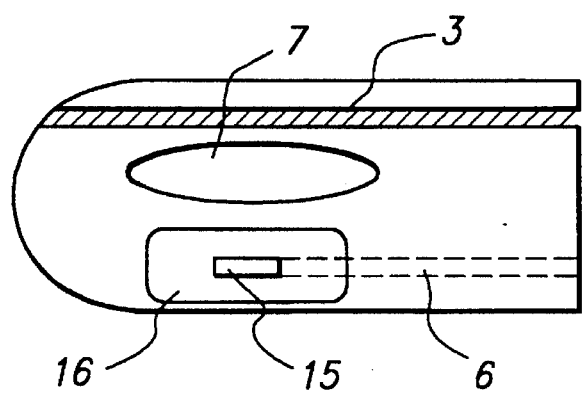
FIG. 3 is a view of the distal end of the catheter shown in FIG. 1.
Figure 5:
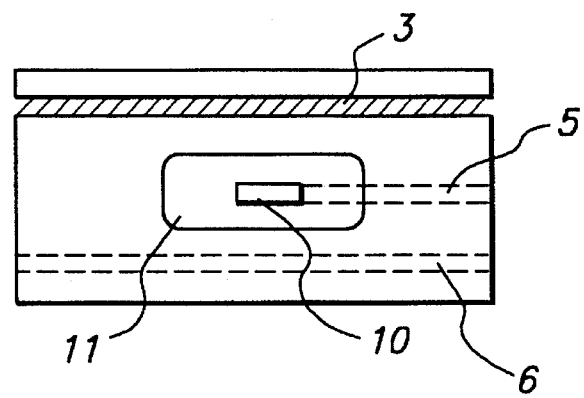
FIG. 5 is a view of a portion of the catheter shown in FIG. 1, depicting the second electrode system of the catheter.

As shown in FIGS. 1–3, catheter 1 is substantially hollow along its length, with the distal end portion thereof being provided with side vents 7 for blood aspiration. Extending within catheter 1, coextensively along its entire length from proximal end 1A to distal end 1B, is a fiber optic cable 3. Preferably, fiber optic cable 3 is retained in position along the inside surface of catheter 1 by being embedded within the polyvinyl chloride or other material from which catheter 1 is fabricated, as shown in FIGS. 2 and 4. The use of fiber optic cable 3 in monitoring oxygen saturation will be described below.

Also extending along the inside surface of catheter 1 are electrical conductors in the form of two copper wires 5 and 6 which are preferably retained in position along the inside surface of catheter 1 in the same manner as fiber optic cable 3, i.e., by being embedded within the polyvinyl chloride or other material from which catheter 1 is fabricated. As shown most clearly in FIGS. 2 and 4, the wires 5 and 6 may desirably be positioned substantially next to each other so as to extend along an inside surface portion of catheter 1 which is substantially opposite fiber optic cable 3. As shown in FIG. 1, electrical wire 5 extends from proximal end 1A of catheter 1 to a first sensor electrode system 10, 11, while electrical wire 6 extends from proximal end 1A to a second sensor electrode system 15, 16 disposed on the angled distal end portion of the catheter.

As shown in FIG. 1, the proximal ends of wires 5 and 6 are provided with electrical couplers 5A and 6A, respectively. The couplers 5A and 6A are adapted to be connected with a differential Wheatstone bridge type detector 20 (FIGS. 1 and 6) as described below. Also provided at proximal end 1A of catheter 1 is a catheter hub 9.

The first and second sensor systems 10, 11 and 15, 16 provided on catheter 1 each comprises an electrochemical sensing system which is sensitive to a predetermined analyte. The first sensor system, disposed on the main axial portion of catheter 1 as shown in FIG. 1, includes a platinum electrode 10 with a hydratable membrane 11 sealed thereover, the membrane containing immobilized reagents or enzymes on its inner surface. Likewise, the second sensor system disposed near the distal end of catheter 1 includes a platinum electrode 15 with a hydratable membrane 16 sealed thereover which contains immobilized reagents or enzymes on its inner surface.

Where the catheter 1 is to be positioned in the hepatic venous system, the membranes 11, 16 are adapted to electrochemically detect analytes specific to the liver. In a preferred embodiment, the specific analyte to be detected is plasma galactose and the membranes 11, 16 comprise galactose oxidase membranes. By way of example, a membrane bound system which may be adapted for use as the first and second sensor systems of a hepatic self-guiding catheter according to the invention is available from Yellow Springs Instruments of Yellow Springs, Ohio. The system is based upon a hydrogen peroxide electrode, having a galactose oxidase membrane for the electrochemical detection of galactose, as follows:

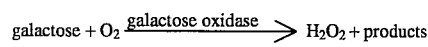

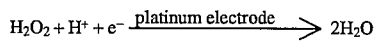

Galactose oxidase in the membrane thus generates hydrogen peroxide from plasma galactose, with the hydrogen peroxide being detected amperometrically in an oxidation-reduction reaction. As noted above and as shown in FIG. 1, the electrical couplers 5A, 6A at the proximal ends of wires 5, 6 are connected to the differential Wheatstone bridge type detector 20 (FIG. 6) which compares the polarographic signal from sensor system 10, 11 vs. that from sensor system 15, 16 and alerts the user, via a visual display and/or an audio signal, when the signals are substantially different.

Where the catheter 1 is to be positioned in the renal venous system, the construction of catheter 1 is substantially the same as described above except that the first and second sensor systems are sensitive to analytes specific to the kidney. In a preferred embodiment, the specific analyte to be detected is creatinine and the membranes 11, 16 comprise creatinine membranes. By way of example, a membrane bound system which may be adapted for use as the first and second electrode systems of a renal self-guiding catheter according to the invention is Kodak Ektachem Chemistry film for the detection of creatinine, as follows:

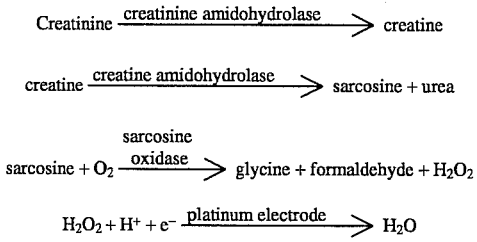

$$H_2O_2 + H^+ + e^- \xrightarrow{\text{platinum electrode}} H_2O$$

The critical feature of the above-discussed analyte detection membranes employed in the self-guiding system of the catheter according to the invention is that they sense analytes or metabolites which are removed from the vascular circuit of interest to a high degree, i.e., in the liver, galactose; and in the kidney, creatinine. The first sensor system 10, 11 will sense the systemic metabolite concentration, while the second or distal sensor system 15, 16 will sense the concentration of the same metabolite in the organ of interest, i.e., the liver or the kidney.

An exemplary use of catheter 1 as a hepatic catheter will now be described with reference to FIGS. 1–5. As an initial procedure, an intravenous galactose infusion is initiated in a patient. This may entail, for example, the infusion of a priming bolus (e.g., 50 to 100 ml) of 5% to 7% galactose, followed by a continuous infusion at 100 ml/hour until a steady-state galactose concentration is reached. Once the intravenous galactose infusion has been initiated, the catheter 1 may be advanced transfemorally through the venous system. As the distal tip 1B reaches the hepatic venous system, it will spontaneously engage the major hepatic veins, i.e., it will spontaneously advance into the hepatic vein when the tip is in proximity thereto. Thus, the distal galactose sensor 15, 16 will be disposed within the hepatic venous system, while the proximal galactose sensor 10, 11 will remain in a vessel outside the hepatic venous system, i.e., in the inferior vena cava in the operable position of catheter 1.

It is known that the extraction fraction of galactose across the splanchnic bed is greater than 90% in normal control subjects and 75% in critically ill septic patients. See Michael S. Dahn, M. Patricia Lange, Robert F. Wilson, Lloyd A. Jacobs, and Robert A. Mitchell, "Hepatic blood flow and splanchnic oxygen consumption measurements in clinical sepsis," *Surgery*, Vol. 107, pp. 295–301 (1990). This large gradient of galactose will be readily detected by a comparison of the polarographic signal from the two sensor systems 10, 11 and 15, 16, by means of the Wheatstone bridge type detector 20. The hepatic venous sensor, i.e., the distal system 15, 16, will detect a low concentration of galactose compared to that detected by proximal sensor system 10, 11 which remains in the inferior vena cava and thus measures systemic, or pre-hepatic galactose levels.

From the foregoing it will be understood that the self-guiding system of catheter 1 permits positioning of the catheter in the hepatic venous system without any need for bedside fluoroscopy or other x-ray devices. By virtue of the angled shape of catheter 1, the angled distal end 1B thereof will spontaneously advance into the hepatic vein when the tip is in proximity to the vein. This positioning of the catheter within the hepatic vein is then readily and immediately confirmed by the large difference in galactose concentrations detected by the two sensor systems provided on catheter 1.

Similarly, where catheter 1 is used in a renal application, the creatinine sensing system as described above will detect a large difference between the creatinine concentration in the renal vein (sensor system 15, 16) and systemic creatinine concentration in the inferior vena cava (sensor system 10, 11). It is known, for example, that substantially 90% of creatinine is extracted across the renovascular circuit. The creatinine concentration detected by sensor system 15, 16 will thus be much lower than that detected by sensor system 10, 11 in the inferior vena cava.

While the sensor systems 10, 11 and 15, 16 have been described as being sensitive to either galactose for liver applications, or creatinine for kidney applications, it will be understood that the sensor systems provided on catheter 1 are not limited to these particular analytes. It is contemplated that the sensor systems may alternatively be adapted to be sensitive to other analytes or metabolites having a significant extraction fraction across the splanchnic bed, renovascular circuit, or other vascular circuit to be explored.

The catheter 1 as described above, in addition to being self-guiding, is capable of performing a number of assessment and monitoring functions. Once the catheter 1 is positioned in the hepatic or renal venous system, direct samples of hepatic or renal venous blood may be taken via catheter 1 for the ex vivo measurement of metabolite concentrations. The catheter 1 is also capable of measuring absolute hepatic or renal blood flow using a tracer clearance technique. For example, if a known infusion rate of galactose is provided (e.g., 100 ml/hour), the data from sensor systems 10, 11 and 15, 16 can be used to calculate hepatic blood flow using a galactose clearance technique, such as described in the aforesaid publication by Dahn et al which is incorporated herein by reference thereto.

Figure 6:
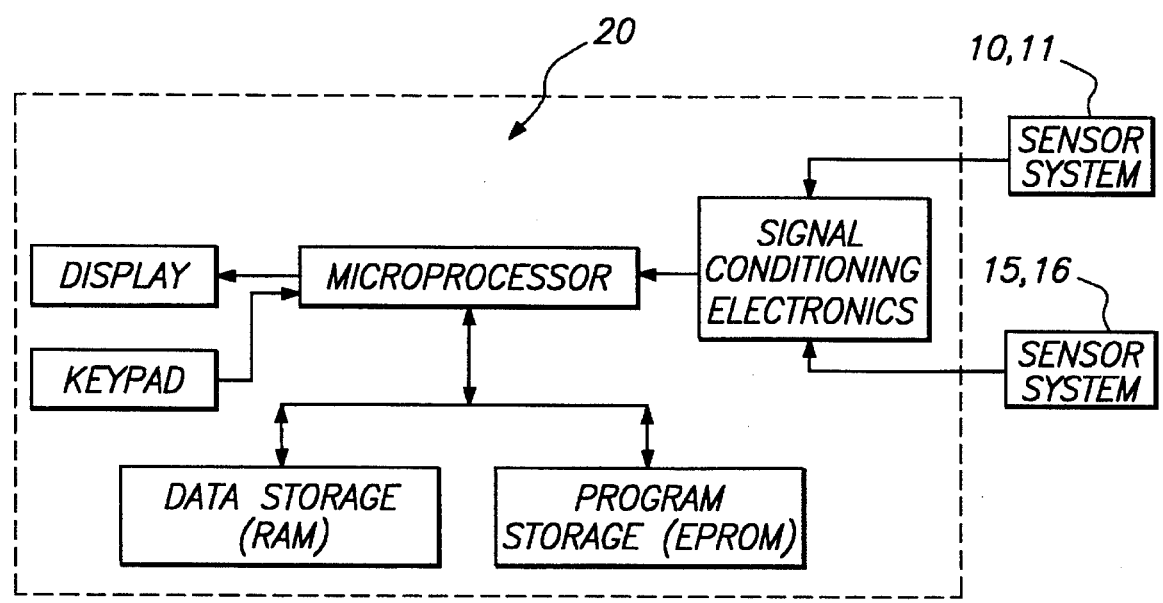
FIG. 6 is a box diagram of a detector for use with the self-guiding and blood flow measuring system of the catheter according to the invention.

As shown in FIG. 6, the Wheatstone bridge type detector 20 as described above may also preferably comprise a microprocessor, program storage memory, and data storage memory. The program storage memory may store one or more equations which permits the microprocessor to calculate galactose concentration values on the basis of signals received from sensor systems 10, 11 and 15, 16, with data being stored in data storage memory and retrievable by the user via a display provided on the detector. Data inputs to be made by the user, such as the galactose infusion rate, may be made via a keypad.

By way of example, the following equation can be used to measure hepatic blood flow ("HBF"):

$$HBF = \frac{\text{Galactose infusion rate}}{SS(EF)}$$

where SS is the net steady-state blood galactose concentration, and EF is the extraction fraction for galactose across the splanchnic bed.

Similarly, the intravenous infusion of inulin and/or para-aminohypurate permits the assessment of glomerular filtration rate and renal blood flow with catheter 1.

In addition, once catheter 1 is positioned in any major hepatic or renal venous vessel, the oxygen saturation in the hepatic or renal venous blood can be continuously monitored via a fiber optic system comprising fiber optic cable 3 and the fiber optic monitor 3A shown in FIG. 1. It will be understood that the fiber optic monitor comprises necessary fiber optic system components including an illumination source, detection means, signal processing means, a microprocessor, etc.

By way of example, fiber optic cable 3 may comprise a fiber optic filament bundle forming part of a commercially-available simple reflectance spectrophotometric system, such as, for example, the system sold under the trademark "OPTICATH" by Oximetrix, Inc. of Mountain View, Calif. In such system, a portion of the fibers in the fiber optic filament bundle function as fiberoptic transmission elements, while the remaining fibers function as receiving elements for reflected and refracted light. The differential wavelength absorption characteristics of hemoglobin in the oxygenated vs. deoxygenated state permit assessment of blood oxygenation based upon light reflected into the receiving filaments. The relative proportion of oxygenated vs. deoxygenated reflected light is electronically processed by the fiber optic monitor to interpret the fraction of oxygen saturation of the hemoglobin in vivo. See John M. Sperinde and Kathi M. Senelly, "The Oximetrix® Opticath® Oximetry System: Theory and Development", Technical Bulletin, Oximetrix, Inc., Mountain View, Calif.

Alternatively, the fiber optic system comprising fiber optic cable 3 and fiber optic monitor 3A may be of the type available from Puritan-Bennett Corporation of Carlsbad Calif. (Model PB3300 Intra-Arterial Blood Gas Monitoring System). In such system, the fiber optic element is coated with a fluorescent dye at the distal end portion. The fluorescence intensity of the dye is related to the ambient oxygen concentration at the catheter tip, so that the reflected fluorescence intensity can be electronically interpreted by processing means in the fiber optic monitor to estimate in vivo oxygen concentration. See Terry Lumsden, William R. Marshall, George A. Divers and Samuel D. Riccitelli, "The PB 3300 intraarterial blood gas monitoring system", *Journal of Clinical Monitoring*, Vol. 10, pp. 59–66 (1994).

It will be understood, however, that the fiber optic system for monitoring oxygen saturation as employed in catheter 1, comprising fiber optic cable 3 and fiber optic monitor 3A is not limited to the foregoing specific systems, and that any suitable fiberoptic system may alternatively be employed.

It is further contemplated that the catheter 1 according to the invention may be provided without the fiber optic cable 3, if desired, so as to provide a self-guiding visceral catheter having all of the above-discussed capabilities except oxygen saturation monitoring.

In addition, a modified embodiment is contemplated in which the self-guiding system of the invention comprises only the sensor electrode system 15, 16, on the angled distal end portion of the catheter, while the sensor electrode system 10, 11 on the main axial portion of the catheter is eliminated. In such a modification, only the concentration of the predetermined analyte (e.g., galactose or creatinine) within the visceral venous system of interest will be sensed, and correct positioning of the distal end of catheter 1 within such system will be confirmed on the basis of a substantial decrease in the predetermined analyte. In other words, when the distal end of catheter 1 enters the visceral venous system, the signals sent to detector 20 by sensor system 15, 16 will reflect a sudden, substantial decrease in the given analyte. Detector 20 would be modified accordingly, i.e., to alert the user to the sudden decrease in analyte concentration by means of a visual and/or audio signal.

While there have been described above what are at present considered to be the preferred embodiments of the invention, it will be understood that various modifications may be made therein without departing from the spirit and scope of the invention. The present embodiments are therefore to be considered in all respects as illustrative, and not restrictive. The scope of the invention is indicated by the appended claims rather than by the foregoing description.

We claim:

1. A visceral catheter, comprising:

a main catheter body having a proximal end and a distal end;

means for guiding said catheter to an operable position in which a portion of said main body is disposed within a predetermined visceral venous system, said guiding means comprising:

first sensor means for detecting values of a predetermined analyte in a vessel disposed outside said visceral venous system in said operable position of said catheter and for outputting signals related thereto, said first sensor means being disposed on a first portion of said main catheter body which remains in said vessel outside said visceral venous system in said operable position of said catheter;

second sensor means for detecting values of said predetermined analyte within said visceral venous system in said operable position of said catheter and for outputting signals related thereto, said second sensor means being disposed on a second portion of said main catheter body which is positioned within said visceral venous system in said operable position of said catheter;

said main catheter body comprising a main axial portion extending from said proximal end and an angled distal end portion extending from said main axial portion, said second portion of said catheter body being disposed on said angled distal end portion of said catheter body;

said predetermined analyte having a specific relationship to an organ associated with said predetermined visceral venous system such that values of said analyte within said visceral venous system are substantially different from systemic values of said analyte outside said visceral venous system; and said first and second sensor means being selectively connected to detector means for comparing said signals from said first and second sensor means and for alerting a user to a substantial difference between said signals.

2. A visceral catheter according to claim 1, wherein:

said angled distal end portion extends from said main axial portion at an acute angle; and said first portion of said catheter body is disposed on said main axial portion of said catheter body.

3. A visceral catheter according to claim 2, wherein:

said angled distal end portion extends from said main axial portion at an angle of substantially 65°.

4. A visceral catheter according to claim 2, wherein:

said first and second sensor means each comprises an electrochemical sensing system including an electrode with a hydratable membrane containing a reagent which detects values of said predetermined analyte.

5. A visceral catheter according to claim 4, wherein:

said predetermined visceral venous system comprises the hepatic venous system;

said predetermined analyte comprises galactose; and said hydratable membrane of said first and second sensor means contains galactose oxidase.

6. A visceral catheter according to claim 4, wherein:

said predetermined visceral venous system comprises the renal venous system;

said predetermined analyte comprises creatinine; and said hydratable membrane of said first and second sensor means contains creatinine amidohydrolase.

7. A visceral catheter according to claim 4, wherein:

said main catheter body is substantially hollow; and said first and second sensor means are selectively connected to said detector means via electrical conductors which extend along an inner surface of said catheter body.

8. A visceral catheter according to claim 4, wherein:

said catheter further comprises means for measuring blood flow in said visceral venous system, said blood flow measuring means comprising said first and second sensor means, and said detector means;

said detector means comprising a microprocessor and program memory, wherein:

said program memory is programmed for computing concentration values of said predetermined analyte, and stores at least one equation for calculating blood flow values based on said concentration values; and said microprocessor receives said signals from said first and second sensor means and utilizes said program memory to calculate concentration values of said predetermined analyte based on said signals from said first and second sensor means, and to calculate said blood flow values utilizing said at least one stored equation and said concentration values.

9. A visceral catheter according to claim 1, wherein:

said catheter further comprises means for monitoring the oxygen saturation of blood in said visceral venous system;

said main catheter body is substantially hollow; and said oxygen saturation monitoring means comprises a fiber optic cable extending along an inner surface of said catheter, substantially from said proximal end to said distal end of said catheter body.

10. A catheter, comprising:

a main catheter body;

first sensor means for detecting values of a predetermined analyte in a vessel disposed outside a predetermined venous system in an operable position of said catheter and for outputting signals related thereto, said first sensor means being disposed on a first portion of said main catheter body which remains in said vessel outside said predetermined venous system in said operable position of said catheter;

second sensor means for detecting values of said predetermined analyte within said predetermined venous system in said operable position of said catheter and for outputting signals related thereto, said second sensor means being disposed on a second portion of said main catheter body which is positioned within said venous system in said operable position of said catheter;

said first and second sensor means being selectively connected to detector means for receiving and processing said signals from said first and second sensor means;

said detector means comprising a microprocessor and program memory, wherein:

said program memory is programmed for computing concentration values of said predetermined analyte; and said microprocessor receives said signals from said first and second sensor means and utilizes said program memory to calculate concentration values of said predetermined analyte based on said signals from said first and second sensor means.

11. A catheter according to claim 10, wherein:

said program memory stores at least one equation for calculating blood flow values on the basis of said analyte concentration values; and said microprocessor calculates said blood flow values utilizing said at least one stored equation and said calculated analyte concentration values.

12. A catheter according to claim 10, wherein:

said main catheter body comprises a main axial portion extending from said proximal end and an angled distal end portion extending from said main axial portion at an acute angle;

said first portion of said catheter body is disposed on said main axial portion of said catheter body; and said second portion of said catheter body is disposed on said angled distal end portion of said catheter body.

13. A catheter according to claim 12, wherein:

said angled distal end portion extends from said main axial portion at an angle of substantially 65°.

14. A catheter according to claim 12, wherein:

said first and second sensor means each comprises an electrochemical sensing system including an electrode with a hydratable membrane containing a reagent which detects values of said predetermined analyte.

15. A catheter according to claim 14, wherein:

said predetermined venous system comprises the hepatic venous system;

said predetermined analyte comprises galactose; and said hydratable membrane of said first and second sensor means contains galactose oxidase.

16. A catheter according to claim 14, wherein:

said predetermined visceral venous system comprises the renal venous system.

17. A visceral catheter, comprising:

a main catheter body;

sensor means for detecting values of a predetermined analyte both within and outside a predetermined visceral venous system and for outputting signals related thereto, said sensor means being disposed on a portion of said main catheter body which, in an operable position of said catheter, is positioned within said predetermined visceral venous system;

said sensor means being selectively connected to detector means for receiving and processing signals from said sensor means;

said predetermined analyte comprising an analyte other than oxygen which has a specific relationship to an organ associated with said predetermined visceral venous system such that values of said analyte within said visceral venous system are substantially lower than systemic values of said analyte outside said visceral venous system; and said detector means processes said signals from said sensor means and alerts a user, by virtue of a substantial decrease in said values of said analyte, when said sensor means is moved from a vessel outside said predetermined venous system to said operable position within said predetermined venous system.

18. A visceral catheter according to claim 17, wherein:

said main catheter body comprises a distal end and a proximal end, with a main axial portion extending from said proximal end and an angled distal end portion extending from said main axial portion at an acute angle; and said sensor means is disposed on said angled distal end portion of said catheter body.

19. A visceral catheter according to claim 18, wherein:

said angled distal end portion extends from said main axial portion at an angle of substantially 65°.

20. A visceral catheter according to claim 17, wherein:

said sensor means comprises an electrochemical sensing system including an electrode with a hydratable membrane containing a reagent which detects values of said predetermined analyte.

* * * * *